US006084971A

United States Patent [19]

McLean

[11] Patent Number: 6,084,971

[45] Date of Patent: Jul. 4, 2000

[54] ACTIVE NOISE ATTENUATION SYSTEM

[75] Inventor: Ian R. McLean, Chatham, Canada

[73] Assignee: Siemens Electric Limited, Ontario, Canada

[21] Appl. No.: 08/872,506

[22] Filed: Jun. 10, 1997

[51] Int. Cl.[7] ........................... A61F 11/06; G10K 11/16; H03B 29/00

[52] U.S. Cl. ......................... 381/71.5; 381/71.7; 381/224

[58] Field of Search ................................. 381/71.1, 71.4, 381/71.5, 71.7, 71.8, 86; 181/224, 222, 206, 228, 198, 202, 229, 282, 255

[56] References Cited

U.S. PATENT DOCUMENTS

| | | | |
|---|---|---|---|
| 3,936,606 | 2/1976 | Wanke . | |
| 4,410,065 | 10/1983 | Harvey . | |
| 4,665,549 | 5/1987 | Eriksson et al. . | |
| 4,876,722 | 10/1989 | Dekker | 381/71.5 |
| 4,947,434 | 8/1990 | Ito | 381/71.5 |
| 5,170,019 | 12/1992 | Lee . | |
| 5,229,556 | 7/1993 | Gaddes . | |
| 5,319,165 | 6/1994 | Geddes . | |
| 5,336,856 | 8/1994 | Krider et al. . | |
| 5,426,703 | 6/1995 | Hamabe et al. . | |
| 5,426,705 | 6/1995 | Yokota et al. . | |
| 5,432,857 | 7/1995 | Geddes . | |
| 5,446,790 | 8/1995 | Tanaka et al. . | |
| 5,457,749 | 10/1995 | Cain et al. . | |
| 5,466,899 | 11/1995 | Geisenberger . | |
| 5,471,537 | 11/1995 | Castwall . | |
| 5,513,266 | 4/1996 | Zuroski . | |
| 5,541,373 | 7/1996 | Cheng . | |
| 5,550,334 | 8/1996 | Langley . | |
| 5,587,563 | 12/1996 | Yazici | 181/224 |
| 5,828,759 | 10/1998 | Everingham | 381/71.5 |

*Primary Examiner*—Minsun Oh Harvey

[57] ABSTRACT

A noise attenuation system for the air induction ducting particularly for an internal combustion engine has an outwardly facing loudspeaker mounted within an air inlet duct so as to lie in the plane of the air intake opening. Signals from an error microphone (and also optionally a detector microphone) are processed in a signal controller, the output driver used to drive the loudspeaker so that a cancellation sound field is produced, which attenuates the noise emanating from the air intake. The speaker is mounted on a fairing body creating an annular flow passage, a filter element ring inserted in the annular space.

24 Claims, 2 Drawing Sheets

ACTIVE NOISE ATTENUATION SYSTEM

BACKGROUND OF THE INVENTION

This invention concerns noise reduction for air induction systems as for internal combustion engines. A portion of the engine noise is propagated back through the air induction system, and in recent years noise attenuation devices have been included in the air induction systems of automotive engines. Such devices have included passive elements such as expansion chambers and Helmholtz resonator chambers connected to air flow ducting in the induction system.

Active devices involving antinoise generators have also been proposed as described in U.S. Pat. No. 5,446,790, issued on Aug. 29, 1995, for an "Intake Sound Control Apparatus". Copending U.S. Ser. No. 08/565,738, filed on Nov. 30, 1995, for a "System and Method for Reducing Engine Noise" describes a compact and efficient packaging of a loudspeaker within an air induction system duct, the loudspeaker driven by an amplified and phase shifted signal received from a microphone positioned to detect noise in an air flow passage.

However, the intensity of the noise reverberating in a confined space within an air duct induction system is considerable, such that it is difficult to control the sound within practical limitations on the power necessary to drive the loudspeaker.

Accordingly, it is the object of the present invention to provide an active noise attenuation system for air induction ducting and particularly in an automotive engine air induction system which requires less power than systems previously proposed for, and in which a more complete cancellation of the noise is radiating from the ducting accomplished.

SUMMARY OF THE INVENTION

The above object is achieved by an active noise attenuation system in which a loud speaker, driven with an amplified out-of-phase signal derived from a signal generated by a microphone in the ducting, is located substantially in the plane of the inlet opening into the air induction system. The loudspeaker is outwardly facing so as to project a sound field which interacts with the sound field of the noise broadcasted out from the inlet opening so as to attenuate or neutralize that sound by an out-of-phase cancellation process.

Since the sound from the engine noise is largely reflected back into the ducting due to the acoustic impedance constituted by the inlet opening, the loudspeaker sound field need interact only with the much smaller proportion of sound emanating from the inlet opening.

By locating the loudspeaker in close proximity to the annular inlet, the monopole-like source of the annular inlet alone is converted into a cylindrical acoustic doublet when the out-of-phase loudspeaker source is activated. The loudspeaker sound field destructively interferes with the sound radiating from the annular inlet such that the coupled impedance of these two noise sources results in a decrease in the net acoustic radiation resistance of the annular inlet. This decrease in the acoustic radiation resistance of the annular inlet results in a decrease in acoustic radiation efficiency and consequently a global reduction in the radiated acoustic power.

The loudspeaker is preferably mounted within a fairing body concentrically disposed in an air duct at the inlet of the air induction system. The loudspeaker faces outwardly and lies substantially in the plane of the inlet opening.

Preferably a first parabolic fairing piece of open cell foam plastic is attached over the loudspeaker, and encloses an error detecting microphone used for feedback of the total radiated sound field. A second aft fairing piece is disposed over an optional noise sensing or detector microphone at the rear of the fairing body. The fairing body may also optionally house an audio amplifier and phase shifting electronics used to drive the loudspeaker.

An annular space is defined between the fairing body and the interior of the duct through which the air flow passes, with the restrictive effect of the system minimized by the streamlining effect of the fairing pieces and a bell mouth configuration of the duct just upstream of the inlet opening.

An annular air filter element may also be optionally installed in the annular space to insure laminar flow and further minimize the restriction to air flow created by the presence of the system.

DETAILED DESCRIPTION

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

Figure 1:
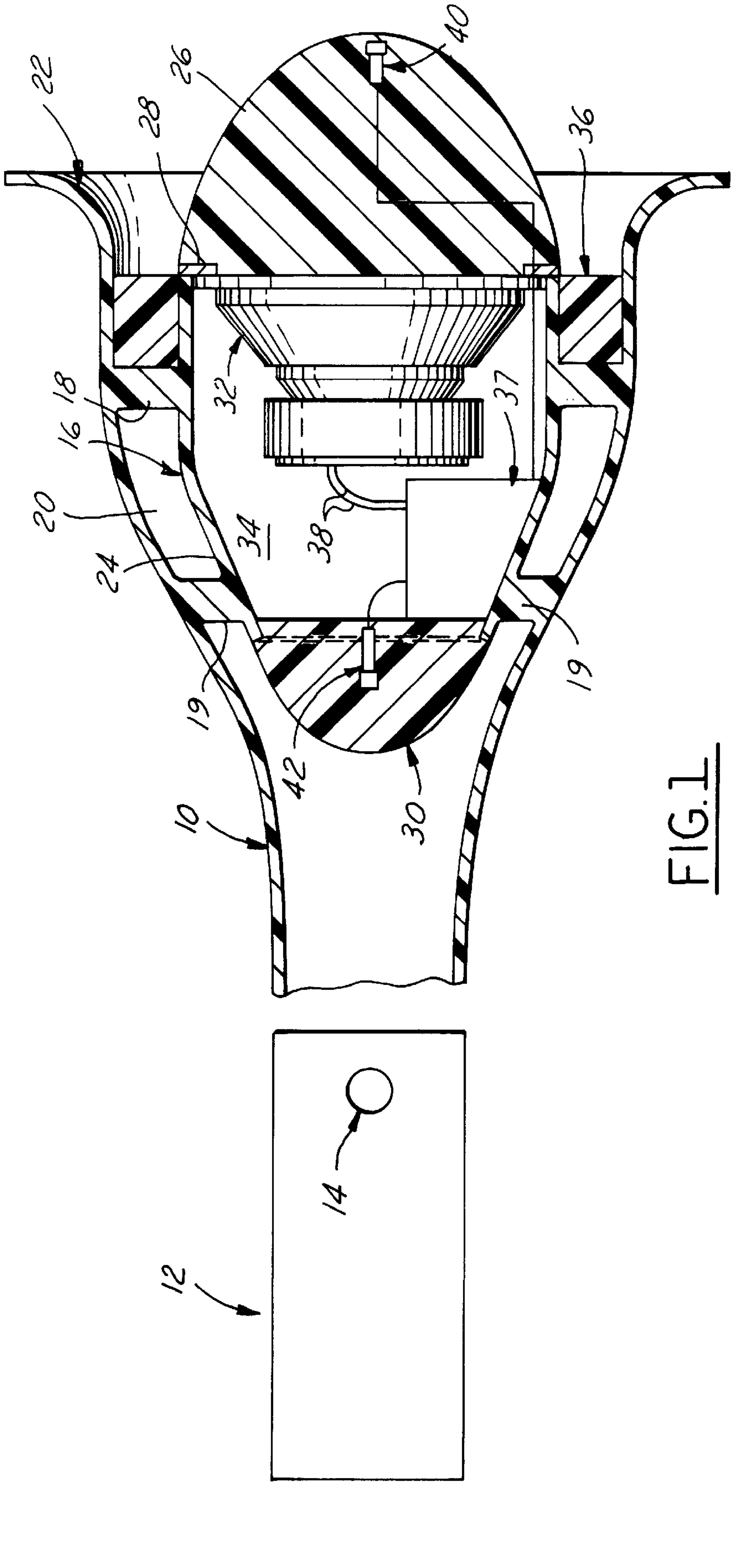
FIG. 1 is a partially sectional view taken lengthwise through an inlet duct section on an engine air induction system having an active noise reduction system installation therein according to the present invention with a diagrammatic representation of the associated engine.

Referring to FIG. 1, an inlet duct section 10 is shown forming a part of an air induction system of an internal combustion engine 12 connected to a throttle body 14 included in the engine air induction system, both indicated diagrammatically.

The inlet duct section 10 outwardly flares to accommodate a fairing body 16 suspended concentrically within the inlet duct section 10 with integral struts 18, 19 arranged about an annular passage 20 defined between the exterior of the fairing body and the interior of the duct section 10.

A flared bell mouth 22 extends from the open end of the air duct section 10.

An annular air filter element 36 is pressed into the annular passage 20.

The fairing body 16 is hollow and generally cylindrical in shape, but with a tapered end 24 disposed downstream within the air inlet duct 10. A forward parabolic fairing piece 26 of open cell foam is attached at the front upstream end 28 of the fairing body 16, while an aft parabolic fairing piece 30, also of open cell foam, is attached to the downstream end of the fairing body 16. Thus, air flow can be drawn into the duct 10 with only a minimal restriction resulting from the presence of the fairing body 16.

A loudspeaker 32 is mounted within the chamber 34 inside the hollow fairing body 16, the loudspeaker 32 facing outwardly and having its cone front located in the plane A (FIG. 3) of inlet opening defined where the annular passage 20 meets the beginning of the bell mouth 22. The fairing piece 26, being of open cell foam, is acoustically transparent to the sound field broadcast by the loudspeaker 32.

The loudspeaker 32 is driven by the output signal generated by the signal controller 37. The signal controller 37 also includes an audio amplifier. The signal controller 37 incorporates adaptive filters which use microphone signals as input in order to generate the required signal input to the loudspeaker. The signal controller can also be housed in the chamber 34, although also alternatively able to be externally mounted as only a wire lead connection 38 therebetween is required.

An error microphone 40 is mounted within the forward fairing piece 26 which senses the composite sound of the noise emanating from both the duct 10 and the loudspeaker 32 and generates electrical signals corresponding thereto. Where a feedback control mode of the loudspeaker output is utilized, only the error microphone signal is required as input to the signal controller 37.

Optionally, a detector microphone 42 may also be provided, connected to the signal controller 37, so that a feed forward control mode of the output of the loudspeaker 32 may be utilized. The signal controller 37 processes the signal input from the microphone 42 and outputs a driving signal to the loudspeaker 32 such that the sound emanating from the loudspeaker 32 is approximately the same amplitude as the noise broadcasted from the duct 10, but phase shifted by approximately 180° with respect to the noise broadcasted from the duct 10 so as to create "cancellation" sounds by the speaker 32.

Figure 3:
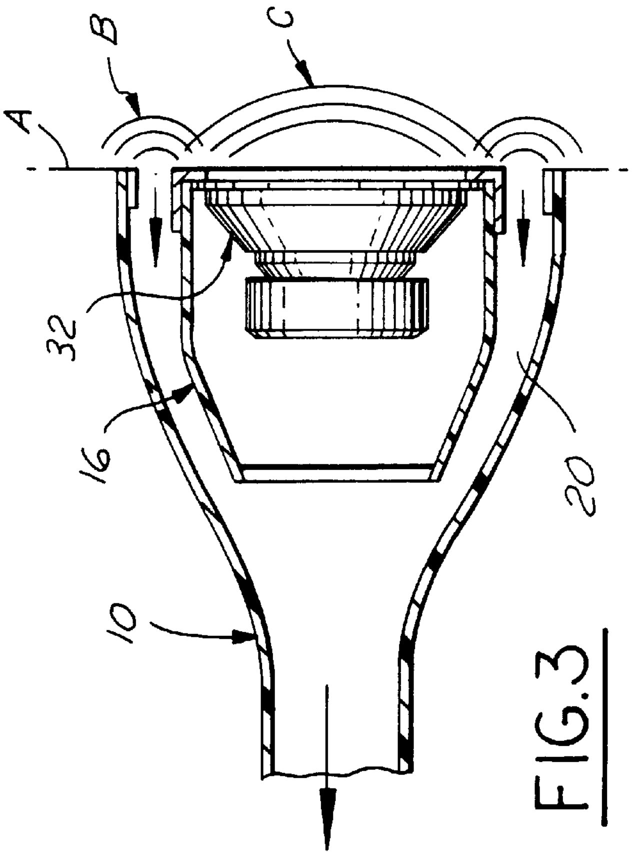
FIG. 3 is a diagrammatic representation of the sound field interaction of the emanating engine noise and loudspeaker sound.
Figure 2:
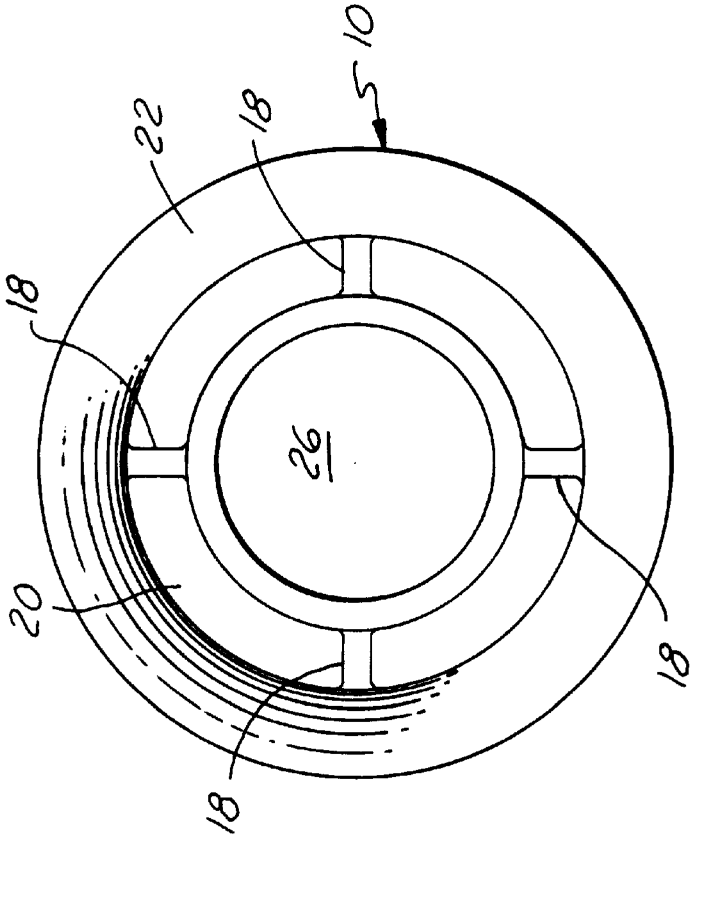
FIG. 2 is an end view of the inlet duct section.

The two sound fields B and C are depicted diagrammatically in FIG. 3 which combine to form an interference pattern in the pressure field associated with a doublet noise source.

Accordingly, an active noise reduction system for air induction system has been provided which is highly efficient and which does not result in an appreciably increased flow restriction presented by the air inlet duct.

What is claimed is:

1. An active noise attenuation system for an air induction system, said system comprising:

an air inlet duct having an open end into which air is drawn;

a fairing body concentrically mounted within said air inlet duct to define an annular flow passage at said open end thereof;

a loudspeaker mounted to be facing outwardly from said air inlet duct and lying substantially in a plane defined by said open end of said air inlet duct;

a sound detector disposed to sense noise from said air inlet duct and produce an electrical signal corresponding thereto; and a signal controller means receiving said electrical signal and amplifying and phase shifting said signal, said amplified and phase shifted signal applied to said loudspeaker to broadcast a sound field within a noise sound field emanating from said annular flow passage, whereby said emanating noise is attenuated by the interaction of said loudspeaker sound field with said emanating noise sound field, further including an air filter ring element inserted in said annular flow passage.

2. The method according to claim 1 wherein the at least one fairing piece is positioned upstream of the loudspeaker.

3. The method according to claim 1 wherein the at least one fairing piece comprising two fairing pieces, one positioned upstream of the loudspeaker, the other positioned downstream of the loudspeaker.

4. The new method according to claim 3, wherein the microphone is disposed within the upstream fairing piece and a second microphone is disposed within the downstream fairing piece.

5. An active noise attenuation system for an air induction system, said system comprising:

an air inlet duct having an open end into which air is drawn;

a fairing body concentrically mounted within said air inlet duct to define an annular flow passage at said open end thereof;

a loudspeaker mounted to be facing outwardly from said air inlet duct and lying substantially in a plane defined by said open end of said air inlet duct;

a sound detector disposed to sense noise from said air inlet duct and produce an electrical signal corresponding thereto; and a signal controller means receiving said electrical signal and amplifying and phase shifting said signal, said amplified and phase shifted signal applied to said loudspeaker to broadcast a sound field within a noise sound field emanating from said annular flow passage, whereby said emanating noise is attenuated by the interaction of said loudspeaker sound field with said emanating noise sound field, further including an open cell foam forward fairing piece mounted to said fairing body and projecting out from said plane of said air inlet.

6. The system according to claim 5 wherein said sound detector comprises a microphone mounted within said forward fairing piece.

7. The method according to claim 6 further including the step of installing an acoustically transparent fairing piece over said speaker to project out therefrom.

8. The method according to claim 6 wherein the at least one fairing piece is positioned upstream of the loudspeaker.

9. The method according to claim 6 wherein the at least one fairing piece comprising two fairing pieces, one positioned upstream of the loudspeaker, the other positioned downstream of the loudspeaker.

10. The method according to claim 9, wherein the microphone is disposed within the upstream fairing piece and a second microphone is disposed within the downstream fairing piece.

11. The system according to claim 5 wherein the fairing piece is of parabolic shape.

12. The method according to claim 11 further including the step of installing an acoustically transparent fairing piece over said speaker to project out therefrom.

13. The method according to claim 11 wherein the at least one fairing piece is positioned upstream of the loudspeaker.

14. The method according to claim 11 wherein the at least one fairing piece comprising two fairing pieces, one positioned upstream of the loudspeaker, the other positioned downstream of the loudspeaker.

15. The method according to claim 14, wherein the microphone is disposed within the upstream fairing piece and a second microphone is disposed within the downstream fairing piece.

16. The method according to claim 5 further including the step of installing an acoustically transparent fairing piece over said speaker to project out therefrom.

17. The method according to claim 5 wherein the at least one fairing piece is positioned upstream of the loudspeaker.

18. The method according to claim 5 wherein the at least one fairing piece comprising two fairing pieces, one positioned upstream of the loudspeaker, the other positioned downstream of the loudspeaker.

19. The method according to claim 18, wherein the microphone is disposed within the upstream fairing piece and a second microphone is disposed within the downstream fairing piece.

20. An active noise attenuation system for an air induction system, said system comprising:

an air inlet duct having an open end into which air is drawn;

a fairing body concentrically mounted within said air inlet duct to define an annular flow passage at said open end thereof;

a loudspeaker mounted to be facing outwardly from said air inlet duct and lying substantially in a plane defined by said open end of said air inlet duct;

a sound detector disposed to sense noise from said air inlet duct and produce an electrical signal corresponding thereto; and a signal controller means receiving said electrical signal and amplifying and phase shifting said signal, said amplified and phase shifted signal applied to said loudspeaker to broadcast a sound field within a noise sound field emanating from said annular flow passage, whereby said emanating noise is attenuated by the interaction of said loudspeaker sound field with said emanating noise sound field, further including an aft fairing piece of open cell foam mounted to the rear of said fairing body and projecting downstream, said sound detector mounted in said aft fairing piece generating feed forward control signals for said signal controller means.

21. The method according to claim 20 further including the step of installing an acoustically transparent fairing piece over said speaker to project out therefrom.

22. The method according to claim 20 wherein the at least one fairing piece is positioned upstream of the loudspeaker.

23. The method according to claim 20 wherein the at least one fairing piece comprising two fairing pieces, one positioned upstream of the loudspeaker, the other positioned downstream of the loudspeaker.

24. The method according to claim 23, wherein the microphone is disposed within the upstream fairing piece and a second microphone is disposed within the downstream fairing piece.

* * * * *